United States Patent [19]
L'Esperance, Jr.

[11] Patent Number: 5,507,741
[45] Date of Patent: Apr. 16, 1996

[54] OPHTHALMIC METHOD FOR LASER SURGERY OF THE CORNEA

[76] Inventor: Francis A. L'Esperance, Jr., 255 Oakwood Rd., Englewood, N.J. 07631

[21] Appl. No.: 146,045

[22] Filed: Jan. 20, 1988

Related U.S. Application Data

[60] Division of Ser. No. 74,580, Jul. 17, 1987, abandoned, which is a continuation-in-part of Ser. No. 891,285, Jul. 31, 1986, Pat. No. 4,732,148, which is a continuation-in-part of Ser. No. 778,801, Sep. 23, 1985, abandoned, which is a continuation-in-part of Ser. No. 742,225, Jun. 6, 1985, abandoned, which is a continuation-in-part of Ser. No. 552,983, Nov. 17, 1983, abandoned.

[51] Int. Cl.$^6$ ........................................ A61B 5/02
[52] U.S. Cl. ................ 606/5; 606/2; 606/3; 219/121.69; 219/121.74
[58] Field of Search ................... 128/303.1, 395, 128/847; 319/121.6, 121.67, 121.68, 121.69, 121.72, 121.73–121.75

[56] References Cited

U.S. PATENT DOCUMENTS

| | | | |
|---|---|---|---|
| 4,156,124 | 5/1979 | Macken | 219/121.6 |
| 4,676,790 | 6/1987 | Kern | 623/5 |
| 4,772,283 | 9/1988 | White | 623/5 |
| 4,856,513 | 8/1989 | Mullen | 128/303.1 |

FOREIGN PATENT DOCUMENTS 8701930  4/1987  WIPO ................... 128/303.1

*Primary Examiner*—David M. Shay
*Attorney, Agent, or Firm*—Hopgood, Calimafde, Kalil & Judlowe

[57] ABSTRACT

The invention contemplates an inventory of disposable elements adapted for selective placement in the path of laser-beam delivery to the cornea. Each of the disposable elements carries a membrane which is opaque to the laser beam and which is designedly subject to ablation when exposed to the laser beam, the thickness of the membrane being a precharacterized function of local area such that a given laser-beam course of exposure will require greater or lesser time to locally ablate the membrane and thus permit laser-beam exposure past the membrane and into correspondingly localized ablating impingement with the cornea. Stated in other words, varying-spot size at the cornea is achieved by a time-release function of the membrane, on a predetermined area-controlled basis that is designed to achieve the diopter change specifically identified with each particular selectable element.

7 Claims, 1 Drawing Sheet

OPHTHALMIC METHOD FOR LASER SURGERY OF THE CORNEA

RELATED CASES

This application is a division of application Ser. No. 074,580, filed Jul. 17, 1987, abandoned and said application is a continuation-in-part of my application Ser. No. 891,285, filed Jul. 31, 1986, now U.S. Pat. No. 4,732,148. Said application is a continuation-in-part of application Ser. No. 778,801, filed Sep. 23, 1985 (now abandoned); said Ser. No. 778,801 is a continuation-in-part of application Ser. No. 742,225, filed Jun. 6, 1985 (now abandoned); and said Ser. No. 742,225 is a continuation-in-part of my original application Ser. No. 552,983, filed Nov. 17 1983, abandoned, which application Ser. No. 552,983 was continued-in-part as Ser. No. 748,358, filed Jun. 24, 1985 (now U.S. Pat. No. 4,665,913). The disclosures of said applications and of other applications identified herein are hereby incorporated by reference.

BACKGROUND OF THE INVENTION

The invention relates to that aspect of ophthalmic surgery which is concerned with operations upon the external surface of the cornea.

Operations of the character indicated include corneal transplants and keratotomies; such operations have traditionally required skilled manipulation of a cutting instrument. But, however keen the cutting edge, the mere entry of the edge into the surface of the cornea necessarily means a wedge-like lateral pressure against body cells displaced by the entry, on both sides of the entry. Such lateral pressure is damaging to several layers of cells on both sides of the entry, to the extent impairing the ability of the wound to heal, and resulting in the formation of scar tissue.

My original patent application Ser. No. 552,983, filed Nov. 17, 1983, includes a background discussion of the effects of various available wavelengths of laser radiation in ophthalmic surgery and, in particular, surgery performed on the anterior surface of the cornea. It is explained that radiation at ultraviolet wavelengths is desirable by reason of its high photon energy. This energy is greatly effective on impact with tissue, in that molecules of tissue are decomposed on photon impact, resulting in tissue ablation by photodecomposition. Molecules at the irradiated surface are broken into smaller volatile fragments without heating the remaining substrate; the mechanism of the ablation is photochemical, i.e., the direct breakdown of intra-molecular bonds. Photothermal and/or photocoagulation effects are neither characteristic nor observable in ablations at ultraviolet wavelengths, and cell damage adjacent the ablation is insignificant.

Said related-case applications deal with various concepts whereby laser radiation at ultraviolet wavelengths of 200-nm or less are controlled in delivery of laser radiation to the visually used area of the anterior surface of the cornea so as to penetrate the stroma and achieve a predeterminable volumetric removal of corneal tissue, thereby so correctively changing the profile of the anterior surface as to reduce a myopia, or a hyperopia, or an astigmatic abnormality which existed prior to such laser surgery.

Said related-case applications also deal with sculpturing penetration of the stroma, and my copending applications Ser. No. 049,333, filed May 13, 1987 and Ser. No. 059,617, filed Jun. 8, 1987, deal with manipulative and other operations upon the cornea in preparation for and in conjunction with sculpturing operations as in said related-case applications. The present application deals with sculpturing per se, and it will be understood that the manipulative and preparatory and other operations of said Ser. Nos. 049,333 and 059,617 are presently preferred in connection with the sculpturing method and means to be described herein.

The sculpturing technique of parent application Ser. No. 891,285 may be briefly stated as involving corneal exposure to a laser beam of varying spot size to achieve an ablated change in anterior-surface curvature in the visually used central area of the cornea. Various means have been described to achieve this result, and most conveniently the previously described means have involved microprocessor means to assure a given exposure program in the course of which spot-size area varies as predetermined to achieve a given profile change.

BRIEF STATEMENT OF THE INVENTION

It is an object of the invention to provide an improved method and means for variable-spot-size laser sculpture of the anterior surface of the cornea to achieve an optical improvement of the involved eye.

A specific object is to achieve the above object with simplified techniques which do not require microprocessor control of spot-size variation.

Another specific object is to achieve the above objects by providing the ophthalmic surgeon with an inventory of differently precharacterized disposable elements which can be selected from inventory in accordance with the optical change to be achieved, so that, for example, the surgeon can select, e.g., in diopter-related increments, for plus or minus spherical change and/or for plus or minus cylindrical change, the change he deems necessary to improve the optical performance of a given eye.

The invention achieves the foregoing objects by providing an inventory of disposable elements adapted for selective placement in the path of laser-beam delivery to the cornea. Each of the disposable elements carries a membrane which is opaque to the laser beam and which is designedly subject to ablation when exposed to the laser beam, the thickness of the membrane being a precharacterized function of local area such that a given laser-beam course of exposure will require greater or lesser time to locally ablate the membrane and thus permit laser-beam exposure past the membrane and into correspondingly localized ablating impingement with the cornea. Stated in other words, varying-spot size at the cornea is achieved by a time-release function of the membrane, on a predetermined area-controlled basis that is designed to achieve the diopter change specifically identified with each particular selectable element.

DETAILED DESCRIPTION

The invention will be described in detail for illustrative embodiments, in conjunction with the accompanying drawings, in which.

Figure 1:
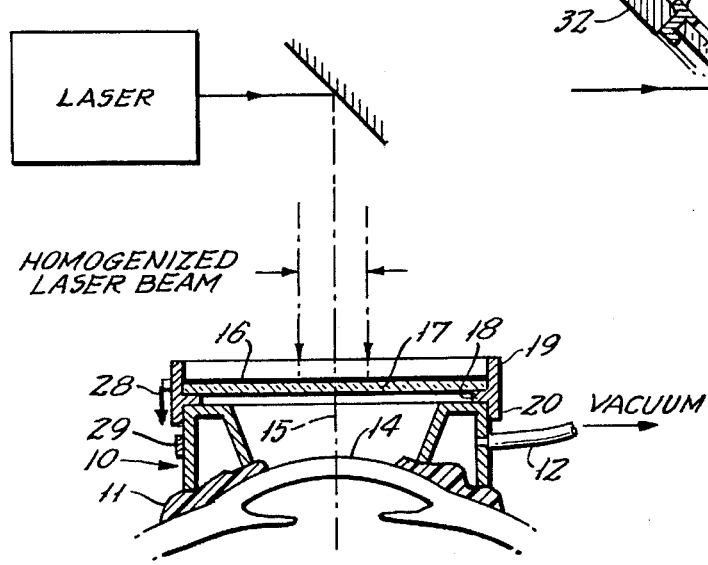
FIG. 1 is a simplified view in vertical section showing means for supporting a selected ablatable membrane element of the invention, for use in laser surgery of a given cornea.
Figure 1A:
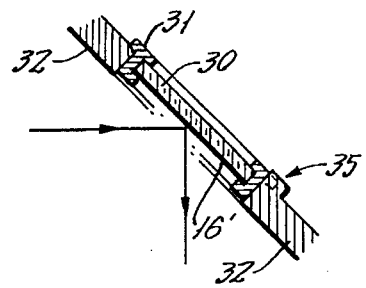
FIG. 1A is a fragmentary sectional view to illustrate a modification.
Figure 2:
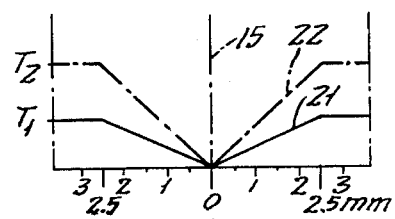
FIG. 2 is a graphical presentation, to differently enlarged and exaggerated abscissa and ordinate scales, to illustrate profiling of ablatable-membrane thickness to achieve a myopia-reducing result in the context of FIG. 1.
Figure 4:
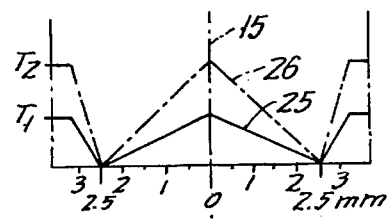
Figure 3:
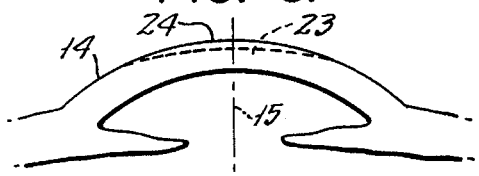
FIG. 3 is a simplified sectional view to illustrate the myopia-reducing sculptured-surface correction achieved with an ablatable-membrane characteristic as in FIG. 2.
Figure 5:
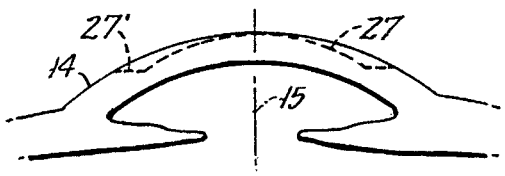
Figure 6:
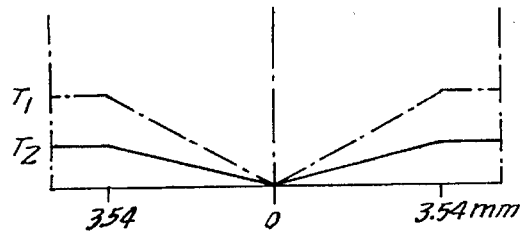
Figure 7:
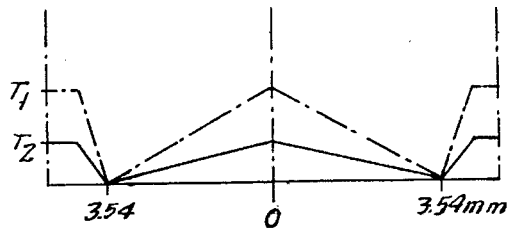

FIGS. 4 and 5 correspond to FIGS. 2 and 3, to illustrate the hyperopia-reducing sculptured-surface correction achieved with an ablatable-membrane characteristic as in FIG. 4; and FIGS. 6 and 7 correspond to FIGS. 2 and 4, to illustrate a relationship in the modification of FIG. 1A.

In FIG. 1, the invention is shown in application to an eye-retaining device 10 which may be as described in U.S. Pat. No. 4,665,913. Device 10 may thus be a hollow annulus, having a convergent axial-end wall 11 of air-permeable material contoured to engage and retain an eye via a scleral-corneal region. A side-port connection 12 to a vacuum pump enables retention of engagement of wall 11 to the cornea 14 to be operated upon, and, optionally, the device 10 may be fixedly referenced to associated laser apparatus (by means not shown).

Preferably and suitably, the laser apparatus is an excimer laser, committed to pulsed ultraviolet radiation at 200 nanometers or less, as for example provided at 193 nm by an argon-fluoride laser. Preferably also, the output beam of the laser is processed for shaping and for homogeneity of flux distribution, for directional projection of a homogenized coherent beam of circular section (e.g., of 5 or 6-mm diameter) that is centrally aligned with the optical axis 15 of the eye. Means for processing the output of an excimer laser to produce such a homogenized beam of circular section are described in detail in copending Telfair, et al. application Ser. No. 009,724, filed Feb. 2, 1987 and therefore need not now be further amplified, being identified by suitable legend in FIG. 1.

In accordance with the invention, an ablatable membrane 16 of suitably precharacterized thickness distribution is selectively positionable in the path of laser beam projection on axis 15. Conveniently, the membrane 16 is a coating on the upper surface of a plane-parallel supporting substrate 17 of material that is transparent to the laser beam; a suitable material for this substrate purpose is a synthetic fused silica (e.g., Suprasil, a commercial product of Heraeus-Amersil), or a fluoride compound, such as calcium fluoride, magnesium fluoride, or barium fluoride. In the form shown, substrate 17 is seated upon the inward annular flange 18 of a ring member 19, which is adapted, via a depending flange 20, for concentric engagement to the circular upper rim edge of the eye-retaining device 10.

The membrane 16 is ablatable under action of the laser beam at a rate which preferably (although not necessarily) corresponds with the rate of laser-beam ablative penetration into the stroma of the cornea. Stated in other words, within the central circular area of laser surgery upon the cornea, the maximum thickness of the ablatable membrane 16 is such that, for the maximum extent of stroma penetration involved in a particular corrective procedure, the surgical exposure can be terminated when the entire maximum thickness of exposed membrane is observed to have been ablatively removed. Suitable materials for the ablatable membrane 16 include polyimide, Mylar and poly(ethylene terephthalate).

FIG. 2 provides illustration of the vertical-section thickness profile for each of two selectively available elements, each of which is configured to effect a myopia reduction. For example, a profile 21 of lesser maximum thickness $T_1$ is seen to reduce from its maximum to zero thickness as a function of decreasing radius about the central axis, for the case of a laser-beam section diameter of 5 mm. And a profile 22 of greater maximum thickness $T_2$ is also seen to reduce from its maximum to zero thickness as a function of decreasing radius about the central axis. The net effective difference between the two profiles is that it will take greater time to reduce the involved central circular area of membrane 16 to a full 5-mm circular bore when membrane 16 is characterized by profile 22, than will be the case when membrane 16 is characterized by the profile 21; this fact translates into accomplishing a greater diopter reduction in cornea curvature for a membrane 16 of thickness profile $T_2$ than is the case for a membrane 16 of thickness profile $T_1$. In both cases, laser-beam exposure should be terminated when the ablated membrane 16 is observed to attain a cylindrical bore, which in the present illustrative case will be of 2.5-mm radius, achieving optical-used curvature correction over a 5-mm diameter. In FIG. 3, the newly achieved curvature correction is suggested by dashed line 23, in relation to the more myopic original profile 24 of the cornea 14.

The thickness profiles 25–26 shown for membrane 16 in FIG. 4 are respectively illustrative of what is needed in maximum membrane (16) thickness (a) to achieve hyperopia reduction of lesser degree, using the lesser maximum thickness $T_1$, and (b) to achieve hyperopia reduction of greater degree, using the greater maximum thickness $T_2$. In the case of the lesser thickness profile 25, thickness is greatest ($T_1$) at the center and is a decreasing function of radius to the point of zero thickness at the outer limit of optical correction (e.g., at 2.5-mm radius); in the case of the greater-thickness profile 26, thickness is also greatest ($T_2$) at the center and is also a decreasing function of radius to the point of zero thickness at the same outer limit of optical correction. If the profiles 25–26 both terminated at the outer limit of optical correction, then the resulting sculpture of cornea 14 would be characterized by a sharply defined outer cylindrical wall, but by utilizing the next 0.5 to 0.75-mm increment of radius to taper membrane thickness back to maximum, i.e., radially outward of the outer limit of optical correction, it is possible to materially reduce the sharp-edge nature of such a wall. The ablation upon the cornea thus produces the hyperopia-reduced profile 27 (FIG. 5) out to the illustrative outer limit of optical correction, and a gently beveled annulus 27' of relatively smooth transition to the remaining outer unexposed area of the cornea. It will be understood that to produce the "beveled" hyperopia-reducing result described in connection with FIGS. 4 and 5, it is necessary to adjust the circular section of the laser beam to a slightly larger diameter (e.g., 6.5 to 7-mm) than for the case of myopia-reduction (FIGS. 2 and 3), but such sectional-area selection is among the capabilities of apparatus described in said Telfair, et al. application Ser. No. 009,724.

The ablatable-membrane technique described for the spherically corrective situations in FIGS. 2–3 and 4–5, respectively, will be seen to be further applicable to achieve cylindrical correction needed for reducing an astigmatism. For example, if FIG. 2 is taken as depicting vertical-section profiles wherein the cylindrical axis of astigmatism correction is normal to and through axis 15 of FIG. 2 and wherein FIG. 2 is no longer understood to depict a thickness profile of revolution, but rather a generally V-shaped channel profile extending along a diametral alignment with respect to ring 19), the described exposure course will achieve a cylindrical reduction of cornea curvature; and if ring 19 is preset in rotation about axis 15 such that the cylindrical reduction is oriented to accord with the diagnosed orientation of the patient's astigmatism, then the astigmatism can be reduced to a prescribed diopter-reducing extent merely by correct selection of the maximum thickness of the thickness-characterized ablatable membrane 16. In FIG. 1, an arrow indicator 28 on ring 19 can be brought by ring rotation into register against an azimuth scale 29 on device 10, to enable precise setting of the orientation for an astigmatism-reducing procedure.

In the embodiments thus far described, the thickness-characterized membrane 16 is designed to achieve varying spot-size transmission of stroma-ablating radiation, via a substrate which is transparent to the involved radiation. And in this situation, it is particularly convenient to embody the substrate and its ablatable membrane in a circular ring which is self-centering with respect to the optical size of the eye. But requisite transparent substrate materials may prove to be relatively expensive.

The fragmentary diagram of FIG. 1A indicates that substrate expense need not be a problem, in the alternative event of using a plane mirror 30 as the substrate which carries a thickness-characterized ablatable membrane 16'. In FIG. 1A, mirror 30 is part of a ring element 31 which is insertably located in a circular opening in supporting frame structure 32, the latter being a fixed attachment to the laser housing. Mirror 30 is shown inclined at 45° to the incident laser beam so as to fold the same for vertically downward surgical delivery to the cornea 14, to the progressively varying spot-size extent determined by ablation of membrane 16' in the course of a given surgical procedure.

Before incidence with the membrane-coated surface of element 31, the laser beam will be understood to be of homogeneously distributed flux density across its circular section, which may again be of 5 or 6-mm diameter for a myopia-reducing procedure. But at incidence with the membrane-coated surface, the area of incidence is an ellipse wherein the minor axis is horizontal; and the thickness profile at the minor axis will be understood to be as depicted in FIG. 2, for a minor-axis extent of 5-mm, the extent shown in FIG. 2. On the other hand, the major-axis extent will be greater, being shown as 7.08-mm in FIG. 6; and the curves 21'–22' of varying thicknesss, for the respective maximum thicknesses $T_1$, $T_2$ in the major-axis section plane of FIG. 6, are seen to follow the profiles 21–22 of FIG. 2 on a correspondingly expanded scale. In any case, the elliptical pattern over which membrane thickness is characterized for myopia reduction in the reflecting situation of FIG. 1A will be understood to proceed from zero thickness at the center of the ellipse to maximum thickness $T_1$ (or $T_2$) at the perimeter of the ellipse. Thus, in the course of a given myopia-reducing surgical procedure, the initially reflected beam will be a central spot of circular section, and this spot will progressively expand as the characterized membrane is progressively ablated, until the full circular section of the incident laser beam is reflected into surgical incidence with the cornea; at this point, the surgical procedure will have accomplished the prescribed myopia reduction at the anterior surface of the cornea.

Since it is important for operation of a reflecting system (as in FIG. 1A) that the elliptical thickness pattern of ablatable membrane 16' be correctively oriented such that the minor axis is horizontal, a keying slot-and-stud engagement is schematically shown at 35 between a point on ring 31 and a reference point on structure 32.

What has been said as to myopia reduction via ablation of a membrane 16' that has been precharacterized in minor-axis and major-axis section planes according to FIGS. 2 and 6, respectively, can also be said for hyperopia reduction when membrane 16' has been precharacterized in minor-axis and major-axis section planes according to FIGS. 4 and 7, respectively. It will be recalled, however, from previous discussion that a slightly larger circular-section laser beam is desired for the hyperopia-reducing procedure, and it can be clearly seen from FIG. 7 that the ultimate sculpture of a bevel 27' is just as possible for the reflecting procedure of variable-spot size irradiation (FIG. 1A) as for the transmitting procedure of FIG. 1.

The described invention will be seen to have achieved all stated objects and to provide methods and means for more readily and economically performing a laser-ablated recurvature of the cornea. The surgeon's inventory of membrane-coated rings 19 (or 31) may be precharacterized by thicknesses and thickness profiles which can be labeled in terms well understood by all ophthalmic surgeons, namely, in diopters or fractions thereof, and qualified as to plus and minus spherical, with or without the cylindrically correcting feature. The rings 19 may be prepared by applying standardized coatings 16 of substrates 17, in thicknesses graduated for successive increments of predetermined ultimate stroma penetrations to achieve given diopter changes; and the uniform-thickness membrane layer may be "cut" to its precharacterizing thickness profile, by laser ablation pursuant to the technique of one or more of the above-noted related cases. For example, under microprocessor control and using the apparatus of FIGS. 8, 9 or 15, 16, respectively, of said Ser. No. 891,285, one may prepare for inventory a plurality of rings 19 having membranes 16 with the FIG. 2 spherical or cylindrical correcting thickness profiles; and by using the apparatus of FIG. 30 of said Ser. No. 891,285, one may prepare for further inventory a plurality of such rings 19 having membranes 16 with the FIG. 4 thickness profiles.

It should be noted that manufacture of thickness-characterized reflection rings 31 for use in FIG. 1A is as simple and straightforward as was the case for transmission rings 19 for use in FIG. 1. Specifically, using the same apparatus of said Ser. No. 891,285 as described for characterizing membrane 16 for myopia reduction or for hyperopia reduction, the only difference is that a uniformly thick ($T_1$ or $T_2$) membrane 16' should be inclined at 45° to the incident homogeneous circular beam when precharacterizing the same. Such inclination will enable automatic development of the described profile, with correct elliptical proportioning and orientation, using the keying reference 35.

However, to manufacture rings 31 which are characterized for astigmatism correction, it is necessary, for use in the reflecting system of FIG. 1A, to prepare a series of rings which have been precharacterized for astigmatism correction at each of a series of quantized increments of azimuthal orientation. For the purpose of such manufacture, the astigmatism-reducing apparatus of FIGS. 15, 16 of said Ser. No. 891,285 is selectively adjustable for azimuth orientation, and is well suited to prepare such a series of rings 31.

The expression "zero thickness", as applied herein to describe one of the limits of precharacterized thickness profiling of membrane 16 (or 16') is to be understood as a convenient way of stating (together with the expression "maximum thickness") the range of thickness variation involved in precharacterization to achieve a given recurvature profile of the cornea. Thus, for certain purposes, it may be further convenient or desirable to avoid a truly zero thickness, as for example to provide such added uniformly distributed thickness of membrane 16 (or 16') beneath the described profiling as to permit the surgeon to perform a testing of a given membrane 16 (or 16'), for example, prior to its use for sculpture of a cornea. A test exposure of the homogenized beam to the thus-characterized membrane could illustratively enable the surgeon to determine, as with his stop watch, the time required to expose to the extent of ablative decomposition of the added uniform-thickness increment, such time being visually observed to terminate upon initial laser-beam emergence at the region of least-thickness of the membrane. When the surgeon determines this time, he has in effect calibrated his inserted membrane for its rate of penetrating ablation of the membrane material, thus establishing whether he has selected an element 19 (or 31) with a membrane having the correct diopter-changing value which he has prescribed, or whether he should achieve the prescription by selecting a different ring 19 (or 31) with a membrane designed for its incrementally greater or lesser diopter-changing property. Alternatively, an element 19 (or 31) having a membrane 16 (or 16') that is characterized by known uniform thickness may be a calibrating device forming part of the surgeon's inventory, in that his timing of his laser's ability to ablate through the full membrane thickness of such an element will enable him to immediately determine the current ablating efficacy of his laser beam, thus enabling his appropriate allowance for a drop in ablating efficacy, merely by selecting for a given sculpturing procedure an element 19 (31) having a thickness-characterized membrane 16 (16') that was designed for a laser diopter-changing property, i.e., of lesser maximum thickness.

What is claimed is:

1. The method of making a precharacterized accessory for use in the path of delivery of an ultraviolet laser beam to perform a curvature-changing sculpture of the anterior surface of a cornea, wherein the accessory comprises a plane-parallel plate of substrate material that is transparent to ultraviolet radiation, and an ablatable membrane layer carried by said plate for expendable use in providing a predetermined ablative sculpture of the optically used central area of the anterior surface of the cornea, said membrane being opaque to ultraviolet radiation and having a central circular area of varying thickness which is a function of radius between central inner and radially outer limits of the circular area, the thickness ranging from zero at one of said limits to maximum at the other of said limits, said membrane being of such maximum thickness within said circular area as to require, for a given intensity of ultraviolet radiation, a predetermined total exposure to achieve total ablation of said maximum thickness, said predetermined total exposure being that which is predetermined to achieve a given maximum stroma-penetration depth for a given sculpturing recurvature of the anterior surface of a cornea exposed to ultraviolet radiation via transmission through said plate; which method comprises preparing said plate with a uniformly thick membrane layer on one plane surface thereof, the material of said membrane layer being opaque to ultraviolet radiation, and exposing a central area of said layer to selective ultraviolet radiation and attendant ablative photodecomposition in a volumetric removal of membrane material and with full depth penetration at one locality within said central area, and essentially zero depth penetration at another locality within said central area, such that a predetermined thickness profile is established between said localities.

2. The method of claim 1, in which the thickness variation ranges from essentially zero thickness at the center of said area, to maximum thickness near the peripheral limit of said central area.

3. The method of claim 1, in which the thickness variation ranges from maximum thickness at the center of said area, to essentially zero thickness near the peripheral limit of said central area.

4. The method of claim 1, in which the thickness variation in said central area ranges from maximum thickness along an alignment through the center and across said central area, to essentially zero thickness at equal and opposite maximum lateral offsets from said alignment.

5. The method of claim 1, in which the thickness variation in said central area ranges from minimum thickness along an alignment through the center and across said central area, to essentially said maximum thickness at equal and opposite lateral offsets from said alignment.

6. The method of making a precharacterized accessory for use in the path of delivery of an ultraviolet laser beam to perform a curvature-changing sculpture of the anterior surface of a cornea, wherein the accessory comprises a substrate having a flat surface which is a reflector of ultraviolet radiation, and an ablatable membrane layer carried by said surface for expendable use in providing a predetermined ablative sculpture of the optically used central area of the anterior surface of the cornea, said membrane being opaque to ultraviolet radiation and having a central elliptical area of varying thickness which is a function of radius between central inner and radially outer limits of the elliptical area, the thickness ranging from zero at one end of said limits to maximum at the other of said limits, said membrane being of such maximum thickness within said elliptical area as to require, for a given intensity of ultraviolet radiation, a predetermined total exposure to achieve total ablation of said maximum thickness, said predetermined total exposure being that which is predetermined to achieve a given maximum stroma-penetration depth for a given sculpturing recurvature of the anterior surface of a cornea exposed to ultraviolet radiation via transmission via reflection from said surface; which method comprises preparing said plate with a uniformly thick membrane layer on said flat surface, the material of said membrane layer being opaque to ultraviolet radiation, and at an acute angle of incidence directionally exposing a central area of said layer to selective ultraviolet radiation and attendant ablative photodecomposition in a volumetric removal of membrane material and with full depth penetration at one locality within said central area, and essentially zero depth penetration at another locality within said central area, such that a predetermined thickness profile is established between said localities, and said angle of incidence being such in relation to the major:minor axis relation of said elliptical area as to determine a circular beam section in the reflection from said elliptical area.

7. The method of claim 1 or claim 6, in which the ultraviolet radiation is characterized by a beam having circular symmetry about a central axis of incidence with said membrane layer.

* * * * *